United States Patent
Butikofer et al.

(10) Patent No.: US 6,741,342 B2
(45) Date of Patent: May 25, 2004

(54) USING A LASER BEAM TO INDICATE ROLLER WEAR

(75) Inventors: Chet M. Butikofer, Meridian, ID (US); Srinivas Guddanti, Boise, ID (US)

(73) Assignee: Hewlett-Packard Development Company, L.P., Houston, TX (US)

(*) Notice: Subject to any disclaimer, the term of this patent is extended or adjusted under 35 U.S.C. 154(b) by 113 days.

(21) Appl. No.: 10/121,149

(22) Filed: Apr. 10, 2002

(65) Prior Publication Data

US 2003/0193665 A1 Oct. 16, 2003

(51) Int. Cl.[7] .............................................. G01N 21/00
(52) U.S. Cl. ..................................... 356/237.1; 356/638
(58) Field of Search ............................... 356/237.1, 638, 356/625

(56) References Cited

U.S. PATENT DOCUMENTS

| | | | | |
|---|---|---|---|---|
| 3,604,940 A | * | 9/1971 | Matthews .................... 356/638 |
| 3,640,109 A | * | 2/1972 | Ashton et al. ............... 356/625 |
| 3,749,500 A | * | 7/1973 | Carlson et al. .............. 356/638 |
| 3,922,094 A | * | 11/1975 | Colding et al. ............. 356/638 |
| 4,031,368 A | * | 6/1977 | Colding et al. ............. 356/638 |
| 4,210,403 A | | 7/1980 | Mazouet et al. .......... 400/196.1 |
| 4,272,202 A | | 6/1981 | Schroeder et al. .......... 400/208 |
| 4,297,045 A | | 10/1981 | Burton et al. ................ 400/641 |
| 4,417,147 A | * | 11/1983 | Faville ........................ 356/638 |
| 4,448,559 A | | 5/1984 | Matsuda et al. ......... 400/637.4 |
| 4,502,804 A | | 3/1985 | Willcox ....................... 400/641 |
| 4,548,523 A | | 10/1985 | McGourty et al. .......... 400/617 |
| 4,576,482 A | * | 3/1986 | Pryor .......................... 356/638 |
| 5,092,695 A | | 3/1992 | Silverman et al. .......... 400/249 |
| 5,533,822 A | | 7/1996 | Tsukada et al. ............. 400/641 |
| 5,660,489 A | | 8/1997 | Ishii et al. ................... 400/641 |
| 5,805,291 A | * | 9/1998 | Calvin et al. ............... 356/638 |
| 5,850,233 A | | 12/1998 | Otsuka et al. ............... 346/136 |
| 6,055,047 A | | 4/2000 | Schweizer et al. ....... 356/237.1 |
| 2002/0186370 A1 | * | 12/2002 | Roesner et al. ............. 356/301 |

* cited by examiner

Primary Examiner—F. L. Evans
Assistant Examiner—Kara Geisel
(74) Attorney, Agent, or Firm—James R. McDaniel

(57) ABSTRACT

This invention relates to the method and apparatus for indicating roller wear in a media handling device. Such structures of this type, generally, employ the use of a laser beam that is located adjacent to the media handling device roller. Initially, the roller material obstructs the laser beam. However, when the roller becomes worn out, the roller material no longer obstructs the laser beam and the beam shines on a piece of reflective material that is illuminated when the laser beam contacts it. This illumination will then be seen from the front of the media handling device, such as through the use of an LED. The laser beam can also activate an optical sensor that relays information to the user.

12 Claims, 2 Drawing Sheets

USING A LASER BEAM TO INDICATE ROLLER WEAR

FIELD OF THE INVENTION

This invention relates to the method and apparatus for indicating roller wear in a media handling device. Such structures of this type, generally, employ the use of a laser beam that is located adjacent to the media handling device roller. Initially, the roller material obstructs the laser beam. However, when the roller becomes worn out, the roller material no longer obstructs the laser beam and the beam shines on a piece of reflective material that is illuminated when the laser beam contacts it. This illumination will then be seen from the front of the media handling device, such as through the use of an LED. The laser beam can also activate an optical sensor that relays information to the user.

DESCRIPTION OF THE RELATED ART

Prior to the present invention, as set forth in general terms above and more specifically below, it is known, in the media handling device art, to make use of a device for determining roller wear. Exemplary of such prior art is U.S. Pat. No. 6,055,047 ('047) to A. Schweizer et al., entitled "Device for Determining the Degree of Wear of a Paper Transport Roller." The '047 reference discloses a paper transport roller which comprises two layers having different degrees of reflection for electromagnetic radiation. When the outer layer is worn, the degree of reflection of the surface of the paper transport roller changes and the user is signaled that paper transport roller must be replaced. However, if a foreign object becomes attached to the transport roller of the '047 reference, this foreign object could adversely affect the reflection characteristics of the device. Also, if the paper transport roller does not wear evenly, one edge of the roller may have a different degree of reflection than the other edge of the roller and, possibly, adversely affect the reflection characteristics of the device. Therefore, a more advantageous paper transport roller wear indication system, then, would be presented if the system did not have to rely on a paper transport roller which comprises two layers having different degrees of reflection.

It is apparent from the above that there exists a need in the art for a paper transport roller wear indication system which is lightweight through simplicity of parts and uniqueness of structure, and which these equals the wear indication characteristics of the known paper transport roller wear indication systems, but which at the same time employs a laser beam which will alert the user to the worn condition of the paper transport roller. It is a purpose of this invention to fulfill this and other needs in the art in a manner more apparent to the skilled artisan once given the following disclosure.

SUMMARY OF THE INVENTION

Generally speaking, this invention fulfills these needs by providing a method for indicating media transport roller wear, wherein the method is comprised of steps of: impinging a coherent light beam upon a side of a media transport roller; and indicating when the media transport roller has worn down to a predetermined amount by causing the coherent light beam to pass over the media transport roller and interacting with a media transport roller wear indicating means.

In certain preferred embodiments, the coherent light beam is a laser beam. Also, the media transport roller wear indicating means includes a piece of reflective material and an LED located on the front of the media handling device which includes the media transport roller. Finally, the method further includes step of tracking the rotations of the media transport roller such that the coherent light beam would not need to be turned on until the media transport roller had completed a predetermined number of rotations.

In another further preferred embodiment, the wear of the media transport roller can be accurately detected so that the user can be alerted that the roller needs to be replaced and/or serviced.

In still another further preferred embodiment, an optical sensor can be utilized to sense the coherent light beam when the media transport roller has worn out. The optical sensor can then send this information to the media transport roller wear indicating means or over the network where the user is alerted of the state of the media transport roller.

The preferred media transport roller wear indicating system, according to this invention, offers the following advantages: lightness in weight; ease of assembly and repair; excellent roller wear indicating characteristics; good stability; good durability; and excellent economy. In fact, in many of the preferred embodiments, these factors of lightness in weight, ease of assembly and repair, excellent roller wear indicating characteristics, and excellent economy are optimized to an extent that is considerably higher than heretofore achieved in prior, known media transport roller wear indicating systems.

The above and other features of the present invention, which will become more apparent as the description proceeds, are best understood by considering the following detailed description in conjunction with the accompanying drawings, wherein like characters represent like parts throughout the several views and in which:

DETAILED DESCRIPTION OF THE INVENTION

Figure 1:
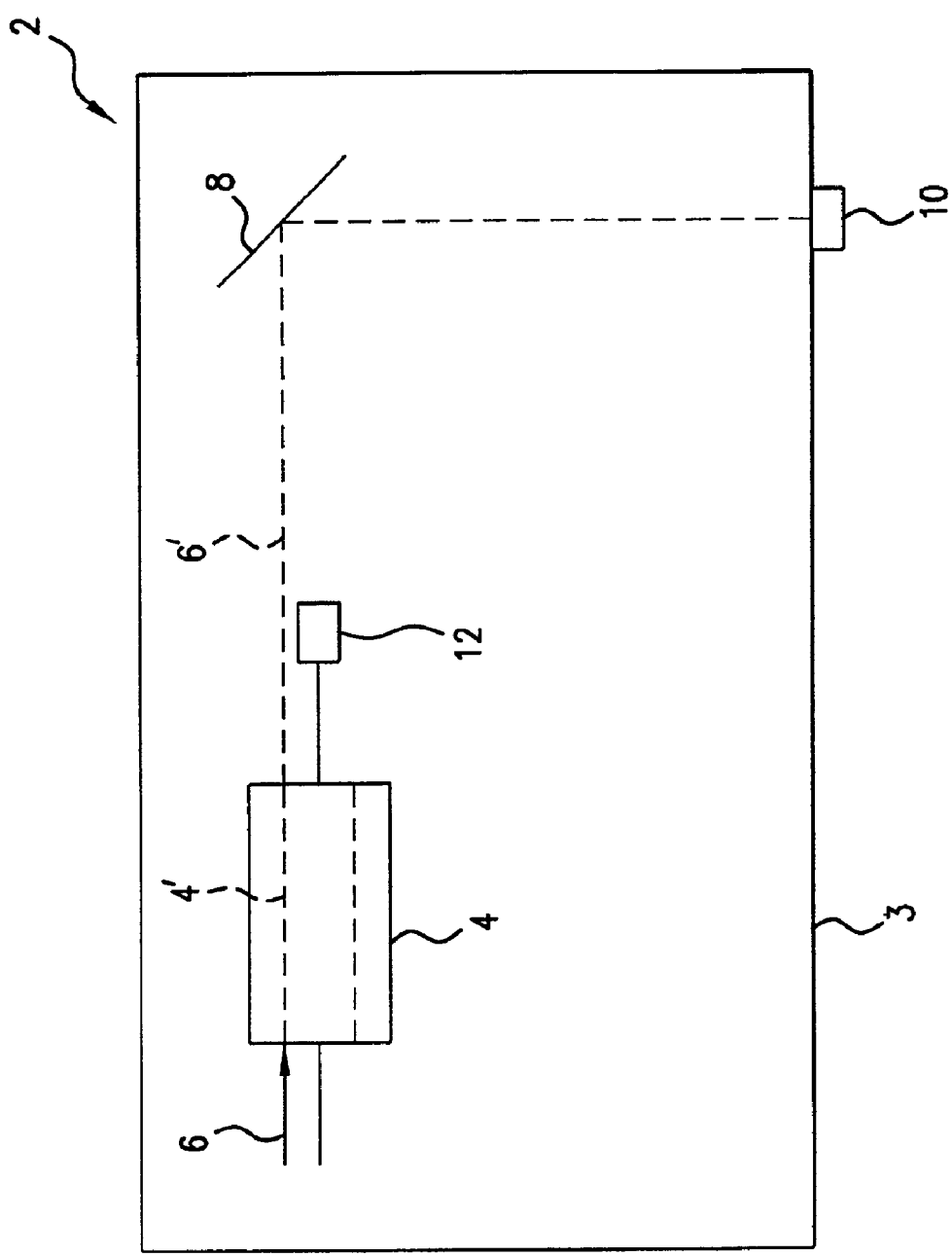
FIG. 1 is a schematic illustration of a media transport roller wear indicating system, according to one embodiment of the present invention.

With reference first to FIG. 1, there is illustrated one preferred embodiment for use of the concepts of this invention. System 2 for indicating media transport roller wear is illustrated in FIG. 1. System 2 includes, in part, media handling device 3, conventional media transport roller 4, subsequent wear level 4', coherent light beams 6 and 6', conventional reflective material 8, media transport roller wear alert 10, and conventional media transport roller rotation counting means 12.

Media handling device 3 can be, but is not limited to, a paper handler, a printer, a copier, a facsimile machine, a printing device or the like. Coherent light beams 6 and 6' are, preferably, laser beams or any other such suitable coherent light beam. However, it is to be understood that coherent light beam 6 can only be powerful enough to impinge upon media transport roller 4 and not adversely affect the physical characteristics of media transport roller 4.

Also, reflective material 8, preferably, is any suitable, durable material that is capable of reflecting coherent light beams 6 and 6' towards media transport roller wear alert 10.

However, it is to understood that the reflective material 8 could be eliminated if coherent beam 6' could directly access media transport roller wear alert means 10.

Media transport roller wear alert 10, preferably, is any suitable device that can interact with coherent light beams 6 and 6' such that when coherent light beams 6 and 6' contact media transport roller wear alert 10, media transport roller wear alert 10 will adequately notify the user of the state of wear of media transport roller 4. For example, media transport roller wear alert 10 can be a LED that changes colors based upon the amount of wear of media transport roller 4. Also, media transport roller wear alert 10 could include a visual display means (not shown) that provides a visual text to the user regarding the wear status of media transport roller 4. It is to be understood that media transport roller wear alert 10 could include an optical sensor (not shown) to sense beam 6' when media transport roller 4 has worn down. Media transport roller alert 10 can then send this information to the user.

Finally, media transport roller rotation counting means 12, preferably, is any suitable, durable device that is capable of counting the number of rotations of media transport roller 4.

During the operation of system 2, a coherent light beam 6 impinges upon a side of media transport roller 4. As can be seen in FIG. 1, as long as media transport roller 4 is not sufficiently worn down to subsequent wear level 4', coherent light beam 6 will not interact with reflective material 8 and media transport roller wear alert 10. In this manner, the user can be assured through media transport roller wear alert 10, such as the showing of a "green" light in transport roller wear alert 10, that media transport roller 4 is not adversely worn.

Once media transport roller 4 has been sufficiently worn down to subsequent wear level 4', coherent light beam 6' passes over media transport roller 4, reflects off of reflective material 8 and interacts with media transport roller wear alert 10. In this manner, the user can be assured through media transport roller wear alert 10, such as showing of a "red" light in media roller wear alert 10, that media transport roller 4 may be suffering from adverse wear and media transport roller 4 may need to be replaced or serviced.

In another embodiment of the present invention, media transport roller rotation counting means 12 can be used to conventionally count the number of rotations of media transport roller 4. In this manner, coherent light beam 6 would not have to be utilized until a predetermined number of rotations of media transport roller 4 have been achieved. This eliminates the need to continuously utilize coherent light beam 6 until needed in system 2.

Figure 2:
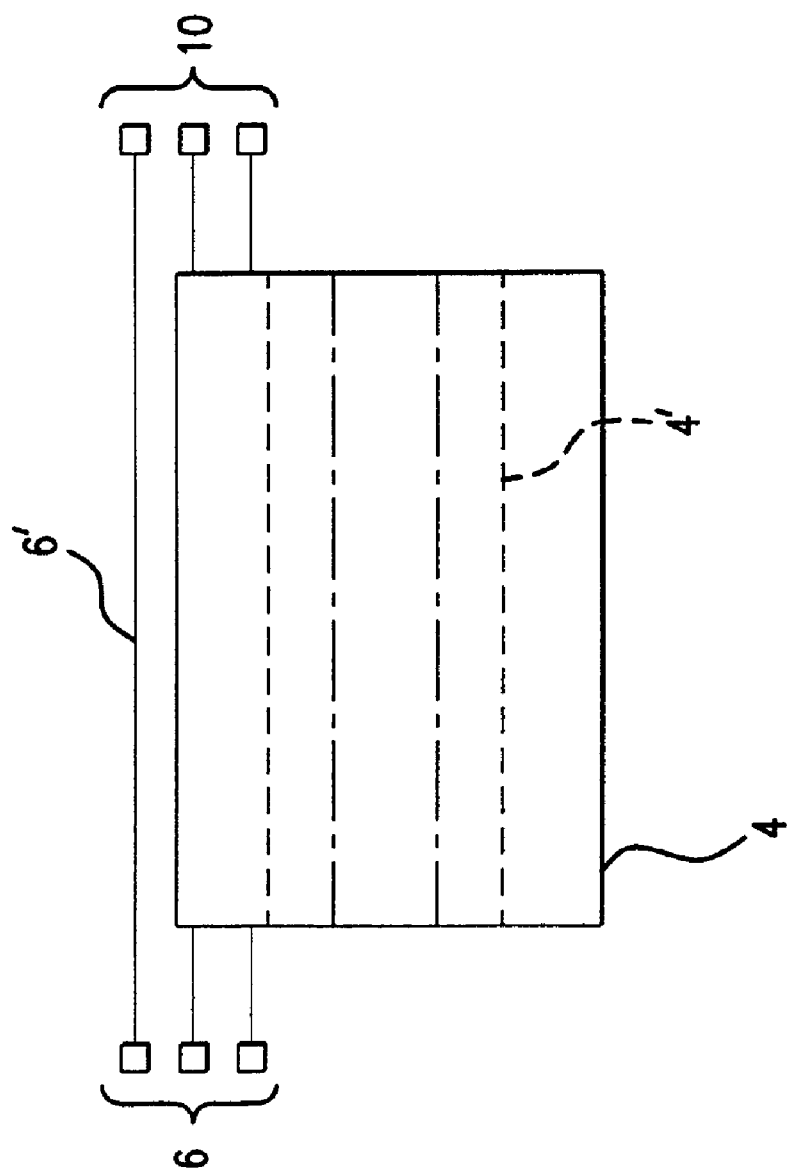
FIG. 2 is a schematic illustration of a media transport roller wear indicating system, according to another embodiment of the present invention.

In still another embodiment of the present invention, a series of coherent light beams 6 and 6' can be utilized to impinge upon media transport roller 4. As shown in FIG. 2, a series of coherent light beams 6 and 6' can be used to inform the user of amounts of wear of media transport roller 4. As can be seen in FIG. 2, each one of the series of coherent light beams 6 and 6' interacts with a separate element of media transport roller wear alert 10. This allows the user to know how much media transport roller 4 has been worn and how long media transport roller 4 is expected to last. It can also be used to warn the user to be ready to replace media transport roller 4 once media transport roller 4 has been sufficiently worn down to subsequent wear level 4'.

Once given the above disclosure, many other features, modifications or improvements will become apparent to the skilled artisan. Such features, modifications or improvements are, therefore, considered to be a part of this invention, the scope of which is to be determined by the following claims

What is claimed is:

1. A method for indicating media transport roller wear comprising the steps of:
    counting a number of rotations of said media transport roller and activating said a coherent light beam when a predetermined number of rotations of said media transport roller have been achieved;
    impinging a coherent light beam upon a side of a media transport roller; and
    indicating when said media transport roller has worn down to a predetermined amount by causing said coherent light beam to pass over said media transport roller and interacting with a media transport roller wear indicating means.

2. The method, as in claim 1, wherein said impinging step is further comprised of the step of:
    continuously impinging said coherent light beam upon said side of said the media transport roller.

3. The method, as in claim 1, wherein said indicating step is further comprised of the step of:
    reflecting said coherent light beam traveling from said media transport roller towards said media transport roller wear indicating means.

4. The method, as in claim 1, wherein said impinging step is further comprised of step of:
    impinging a plurality of coherent light beams upon said side of said media transport roller.

5. The method, as in claim 1, wherein said indicating step is further comprised of the step of:
    operating a light means to indicate a wear status of said media transport roller.

6. A system for indicating media transport roller wear, comprising:
    a media transport roller;
    a media transport roller rotation counting means operatively connected to said media transport roller for activating a coherent light beam when a predetermined number of rotations of said media transport roller have been achieved;
    a first light means for impinging a coherent light beam upon a side of said media transport roller, and
    a media transport roller wear indicating means operatively connected to said first light means.

7. The system, as in claim 6, wherein said system is further comprised of:
    a light beam reflection means located substantially between said media transport roller and said media transport roller wear indicating means.

8. The system, as in claim 7, wherein said light beam reflection means is further comprised of: a piece of reflective material.

9. The system, as in claim 6, wherein said media transport roller wear indicating means is further comprised of:
    a second light means.

10. The system, as in claim 6, wherein said first light means is further comprised of:
    a laser.

11. The system, as in claim 9, wherein said second light moans is further comprised of:
    a light means that changes colors based upon a wear status of said media transport roller.

12. The system, as in claim 6, wherein said first light means is further comprised of:
    a plurality of coherent light beams.

* * * * *

UNITED STATES PATENT AND TRADEMARK OFFICE
CERTIFICATE OF CORRECTION

PATENT NO. : 6,741,342 B2
DATED : May 25, 2004
INVENTOR(S) : Chet M. Butikofer et al.

It is certified that error appears in the above-identified patent and that said Letters Patent is hereby corrected as shown below:

Column 3,
Line 1, after "to" insert -- be --
Line 67, after "claims" insert -- . --

Column 4,
Line 5, after "activating" delete "said"
Line 60, delete "moans" and insert therefor -- means --

Signed and Sealed this

Nineteenth Day of April, 2005

JON W. DUDAS
*Director of the United States Patent and Trademark Office*